United States Patent
Stoltz et al.

(10) Patent No.: US 8,288,353 B2
(45) Date of Patent: *Oct. 16, 2012

(54) METHOD FOR RESTRUCTURING THE EPIDERMIS USING A POLYOL-GLYCOSIDE COMPOSITION

(75) Inventors: Corinne Stoltz, Thiais (FR); Christine Garcia, Castres (FR); Jean-Pierre Boiteux, Saix (FR); Herve Rolland, Castres (FR); Guy Tabacchi, Paris (FR); Alain Milius, Nice (FR)

(73) Assignee: Societe d'Exploitation de Produits pour les Industries Chimiques SEPPIC, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/031,681

(22) Filed: Feb. 22, 2011

(65) Prior Publication Data

US 2011/0144316 A1  Jun. 16, 2011

Related U.S. Application Data

(62) Division of application No. 10/513,643, filed as application No. PCT/FR03/01364 on Apr. 30, 2003, now Pat. No. 8,088,742.

(30) Foreign Application Priority Data

May 7, 2002 (FR) ..................... 02 05681

(51) Int. Cl.
*A01N 43/04* (2006.01)
*A01N 31/00* (2006.01)
*A61K 31/70* (2006.01)
*A61K 31/045* (2006.01)
*C07H 1/00* (2006.01)
*C07H 15/04* (2006.01)

(52) U.S. Cl. .......... 514/23; 514/738; 536/1.11; 536/120
(58) Field of Classification Search .................... 514/23, 514/738; 536/1.11, 120
See application file for complete search history.

(56) References Cited

U.S. PATENT DOCUMENTS 5,814,310 A  9/1998  Nagy et al.
5,891,854 A  4/1999  Thiem et al.

FOREIGN PATENT DOCUMENTS

| EP | 0770378 | 5/1997 |
| FR | 2730409 | 8/1996 |
| JP | 10-158151 | 6/1998 |
| WO | 9625142 | 8/1996 |

OTHER PUBLICATIONS

Machine translation of JP 10-158151 (1998) [online] [Retrieved Jan. 18, 2010] Retrieved from the internet <http://dossier1.ipdl.inpit.go.jp/AIPN/odse_top_dn.ipdl?N0000=7400>.*
Matsumura, S., Imai, K., Yoshikawa, S., Kawada, K., Uchibori, T. (1990) Surface Activities, Biodegradability and Antimicrobial Properties of n-Alkyl Glucosides, Mannosides and Galactosides. Journal of the American Oil Chemists' Society, vol. 67, No. 12, p. 996-1001.*
Lower, E. (1997) The cosmetic advantages of polyglycerols. Manufacturing Chemist, vol. 68, No. 11, p. 30-32.*
International Search Report for PCT/FR03/01364, dated Nov. 13, 2003.
Database CA 'en ligne!; Chemical Abstracts Service, Columbus, Ohio, US; Matsuzawa, Sachiyo et al.: "Moisturizing cosmetics containing saccharides" retrieved from STN Database accession No. 127:23570, XP002229201; and JP 09 077650, Ajinomoto Co., Inc., Japan, Mar. 25, 1997.
Database CA 'en ligne!; Chemical Abstracts Service, Columbus, Ohio, US; Uehara, Shizuka et al.: "Rough skin-preventing and anti aging cosmetics" retrieved from STN Database accession No. 132:283941 XP002229202; and JP 2000 119155, Kosei Co., Ltd., Japan, Apr. 25, 2000.
Patent Abstracts of Japan, vol. 012, No. 283 (C-518), Aug. 3, 1998, and JP 63 063390, Kao Corp, Mar. 19, 1988.
Database WPI, Section Ch, Week 197744, Derwent Publicaitons, Ltd., London, GB; AN 1977-78724Y, XP 002229203; and JP 52 114027, Iizuka), Sep. 24, 1977.

* cited by examiner

*Primary Examiner* — Scarlett Goon
(74) *Attorney, Agent, or Firm* — Yonug & Thompson

(57) ABSTRACT

A method for restructuring the epidermis with a composition, wherein said composition includes a polyol-glycoside and said polyol-glycoside is obtained by the acetalization of a polyol with a reducing sugar.

2 Claims, No Drawings

METHOD FOR RESTRUCTURING THE EPIDERMIS USING A POLYOL-GLYCOSIDE COMPOSITION

This application is a divisional of co-pending application Ser. No. 10/513,643 filed on Dec. 12, 2005, which is the 35 U.S.C. §371 national stage of International PCT/FR03/01364 filed on Apr. 30, 2003, which claims priority to French Application No. 02/05681 filed on May 7, 2002. The entire contents of each of the above-identified applications are hereby incorporated by reference.

The present invention relates to novel polyol-glycoside compositions for topical use.

The invention is of use preferably in the cosmetics field, but also in the dermopharmaceutical or pharmaceutical field, in the field of the textile industry, for example for treating woven or knitted, synthetic or natural textile fibers, or else in the field of the papermaking industry, for example for manufacturing paper for sanitary or domestic use.

The expression "for topical use" used in the context of the present description is therefore understood, in its widest sense, to denote any direct applications (in the case of a cosmetic, dermopharmaceutical or pharmaceutical product) or indirect applications (in the case of textile fibers or of paper) of a composition to the skin or the mucous membranes.

In its direct applications to the skin, the invention is directed more specifically toward compositions for improving the integrity of the skin by providing skin comfort.

The expression composition or substance capable of improving the "integrity of the skin" denotes any composition or substance having moisturizing properties resulting in particular from an ability to reinforce the epidermal moisture content by promoting in particular the synthesis of glycosaminoglycans and/or restructuring properties resulting in particular from an ability to increase the cellular cohesion of the skin by stimulating the synthesis of epidermal ceramides.

It is known that cosmetic compositions generally contain moisturizing substances, such as in particular polyols, ethoxylated polyols or hydrolyzed proteins.

Among the polyols, it is glycerol (polyol comprising three hydroxyl groups) which exhibits the highest moisturizing capacity. However, it has been noted that, at high dose, this can cause certain irritations of the skin and of the mucous membranes in particularly sensitive individuals.

The search for novel moisturizing substances that are tolerated better than glycerol has in particular led to the use of some of its derivatives such as in particular its acetals resulting from condensation with a reducing sugar.

These derivatives which effectively exhibit better skin tolerance than glycerol are characterized, however, by a moisturizing capacity that is generally lower than said glycerol.

Among the glycerol acetals, the products of acetalization of glycerol and of glucose described in document EP 0 770 378 appeared, up until now, to provide the best compromise between moisturizing capacity and skin tolerance.

It has been discovered, unexpectedly, and this constitutes the basis of the present invention, that the glycosides obtained by acetalization of certain polyols containing at least 4, and preferably 4 or 5, hydroxyl functions exhibit better moisturizing properties than the products described in document EP 0 770 378, while at the same time having identical skin tolerance.

This discovery is all the more surprising for going against a preconceived idea, since those skilled in the art know that the moisturizing capacity of polyols decreases when the number of hydroxyl functions increases.

In addition, it has been observed, entirely surprisingly, that the abovementioned glycosides exhibit notable restructuring properties resulting in particular in a better ability to increase the cellular cohesion of the skin than glycerol.

Thus, according to a first aspect, a subject of the present invention is novel compositions for topical use, characterized in that they contain an effective amount of a polyol-glycoside obtained by acetalization of a polyol of formula:

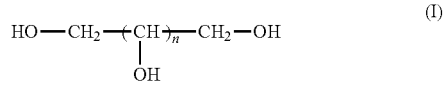

in which n is an integer equal to 2, 3 or 4; or

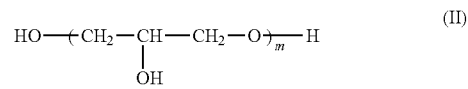

in which m is an integer equal to 2 or 3, with a reducing sugar, it being understood that the polyol-glycoside is not mannosyl erythritol.

The expression "effective amount" used in the context of the present application signifies an amount that is sufficient to provide the composition with a moisturizing and/or restructuring activity on the epidermis.

The polyol-glycosides currently preferred in the context of the invention are those obtained from a reducing sugar such as, for example: glucose, fructose, galactose, maltose, maltotriose, lactose, cellobiose, mannose, ribose or xylose. Among these compounds, glucose, fructose, galactose, maltose, maltotriose, lactose, cellobiose, ribose and xylose are more particularly preferred. Among the latter compounds, glucose, xylose and arabinose are most particularly preferred.

Advantageously, the polyol of formula (I) or (II) mentioned above is chosen from erythritol, xylitol and diglycerol.

The xylityl glucoside constitutes the compound that is currently preferred in the context of the invention.

The compositions for topical use according to the invention can be used in many fields.

According to a particular characteristic, these compositions will be chosen from a cosmetic composition, a dermopharmaceutical composition, a pharmaceutical composition, and an impregnating composition for towelettes.

According to a second aspect, a subject of the present invention is the use of a polyol-glycoside as defined above as an agent for moisturizing the upper layers of the epidermis, or as an agent for restructuring the epidermis.

The polyol-glycosides, the use of which is recommended according to the present invention for preparing compositions for topical use, can be obtained by various synthetic pathways.

A first pathway, referred to as "one-pot synthesis", consists in introducing a reducing sugar and a polyol of formula (I) or (II) into a reactor, according to a controlled stoichiometric ratio, and in subjecting this mixture to an acetalization reaction under predetermined temperature and partial vacuum conditions, in the presence of an acid catalytic system.

The components of this acid catalytic system will generally be chosen from sulfuric acid, hydrochloric acid, phosphoric acid, nitric acid, hypophosphorus acid, methanesulfonic acid, para-toluenesulfonic acid, trifluoromethanesulfonic acid and acid ion exchange resins.

The acetalization reaction will usually be carried out at a temperature of 70 to 130° C., under a vacuum of 300 to 20 mbar.

A second synthetic pathway consists in:
a) subjecting the polyol of formula (I) or (II) to a dehydration, in the presence of an acid catalytic system, at a temperature of between 70° C. and 130° C., under partial vacuum, with concomitant elimination of the water formed during the intramolecular rearrangement undergone by the polyol; then
b) acetalizing the dehydrated polyol thus obtained, by dispersion of a reducing sugar in the reaction medium and by maintenance thereof at a temperature of between 80° C. and 130° C., under partial vacuum.

The acid catalytic system used in this second synthetic pathway may be identical to that mentioned for the first pathway.

A third synthetic pathway by means of trans-acetalization consists in:
a) preparing butylglucoside by reaction between butanol and glucose in the presence of an acid catalytic system, at a temperature of between 90° C. and 105° C., under partial vacuum, with concomitant elimination of the water formed during the reaction; and
b) adding a polyol of formula (I) or (II) to the reaction medium thus obtained, with evacuation by distillation under vacuum of the residual butanol, of the butanol formed during the trans-acetalization reaction and of the water possibly generated during the intramolecular rearrangement of said polyol.

The polyol-glycosides that are useful in the context of the present invention are stable and water-soluble products.

Consequently, they can be incorporated into any type of formulation intended for topical use, or alternatively into any type of support intended to be brought into contact with the skin (paper, towelette, textile, transdermal device, etc.).

In particular, these products can be formulated in the form of a solution, of an emulsion or of a micro-emulsion of the water-in-oil (W/O) or oil-in-water (O/W) type, of a multiple emulsion of the water-in-oil-in-water (W/O/W) or oil-in-water-in-oil (O/W/O) type, of a gel, of an aqueous dispersion, of a solid stick, of an ointment or of an aerosol, or else in anhydrous form, such as a powder.

These products may also be encapsulated, for example in collagen networks or other usual encapsulation substances, such as, for example, in the form of cellulose encapsulations, in gelatin, in wax matrices or in liposomes.

The polyol-glycosides that are useful in the context of the present invention exhibit notable moisturizing properties and make it possible in particular to reinforce the epidermal moisture content and to promote the synthesis of glycosaminoglycans.

The polyol-glycosides that are useful in the context of the present invention also exhibit notable restructuring properties and make it possible in particular to increase the cellular cohesion of the skin. Epidermal lipids represent 10 to 12% of the weight of the dry epidermis. They are involved in the permeability of the stratum corneum, in the phenomenon of desquamation and in the regulation of water fluxes in the skin. Ceramides are the essential lipid components of the stratum corneum, in particular ceramide 1, ceramide 3, ceramide 2, ceramide 4, ceramide 5 and ceramide 6. More precisely, modifications in the amount and in the distribution of the ceramides are observed in a large number of skin pathologies, in particular those associated with disorders of keratinization and of moisturization of the skin: psoriasis, atypical dermatosis, ichthiosis, Sjogren-Larsson syndrome, xerosis and eczema.

The novel compositions containing the polyol-glycosides that are useful in the context of the present invention make it possible to significantly increase the neosynthesis of epidermal ceramides, more precisely of ceramide 1 and of ceramide 2. This increase is surprising in nature in the sense that it is not observed under identical experimental conditions with glycerol.

Consequently, these products may be used in any type of application where a moisturizing and/or restructuring action on the epidermis is desired, for example for face or body care. They may also be used in aqueous systems or compositions of surfactants intended for cleansing the skin and for washing the hair.

The polyol-glycosides that are useful in the context of the present invention will generally be used alone or in combination with other active principles at a dose of approximately 0.01% to 30% by weight, preferably of 0.1 to 10% by weight, in cosmetic or dermopharmaceutical formulations having moisturizing and/or restructuring activity.

These formulations may be anti-aging, restructuring, stimulating, free-radical scavenger, antioxidant, anti-dandruff, anti-acne, calming, anti-neuromediator, anti-Substance P, anti-allergic, pain relief, anti-stress, anti-wrinkle, pro-firmness, pro-elasticity, cicatrizing, toning, tensioning, slimming, veinotonic, draining, anti-redness, immunomodulatory, lightening or revitalizing formulae, or else formulae intended to improve the complexion of the skin, to stimulate the cells or to promote the synthesis of the proteins of the skin, such as collagen or keratin.

The formulations having moisturizing and/or restructuring activity on the epidermis which incorporate a polyol-glycoside according to the invention may be prepared by the methods conventionally used by those skilled in the art in the cosmetology field or in the dermopharmacy field.

The polyol-glycosides according to the invention are particularly useful for tired skin since they introduce the elements necessary for cellular dynamism and for maintaining the functions of the skin. In addition, they stimulate cell regeneration, allowing the skin to become radiant and fresh again.

These polyol-glycosides can also be used in formulae intended to improve cellular exchanges or the condition of the dermal-epidermal junction, or else in sun products, makeup products, such as lipsticks, rouges, powders, or in products for treating or coloring the hair.

These polyol-glycosides may be combined with all types of adjuvants normally used in formulations for topical use, in particular cosmetics or dermopharmaceutical formulations, such as, for example, fatty substances, organic solvents, thickeners and gelling agents, softeners, antioxidants, opacifiers, stabilizing agents, foaming agents, fragrances, ionic or nonionic emulsifiers, mineral fillers, sequestering agents, chelating agents, preserving agents, chemical or mineral screening agents, essential oils, coloring materials, pigments, hydrophilic or lipophilic active agents, lipid vesicles, etc.

Among the oils which may be combined with these polyol-glycosides, mention may be made of paraffins, isoparaffins, white mineral oils, plant oils, animal oils, synthetic oils, silicone oils and fluoro oils.

Among the other fatty substances that can be combined with these products, mention will be made of fatty alcohols or fatty acids, waxes and butters.

Among the emulsifiers that can be combined with these products, mention will be made of the alkyl-polyglycosideand fatty alcohol-based compositions described in U.S. Pat. Nos. 5,958,431, 6,353,034, 5,888,482, 6,268,400 and 5,670,471.

Among the gelling agents or thickeners that can be combined with these products, mention will be made of polymers of natural origin such as xanthan gums, polysaccharides, polymers of synthetic origin such as carboxyvinyl polymers (Carbomer™), acrylic copolymers, polyacrylamides or other polymers provided in an inverse emulsion and described in U.S. Pat. Nos. 6,197,287, 6,346,239, EP 1 056 805, EP 1 166 771, EP 1 152 023 and EP 1 152 022, polyoxyethylenated sugar derivatives (ethoxylated methylglucose), mixed silicates of aluminum-magnesium and of sodium-magnesium.

Among the foaming agents that can be combined with these products, mention will be made of betaines, sulfobetaines, alkylpolyglucosides, lipoamino acids, lipopeptides, sodium lauryl ether sulfate, alkyl sulfates, alkyl ether sulfates, alkyl ether carboxylates, lipoprotein derivatives, protein derivatives, imidazolines and sulfosuccinates.

Among the active principles that can be combined with the moisturizing polyol-glycosides of the invention in order to potentiate their properties, mention will be made, for example, of any active agent already exhibiting moisturizing properties, or alternatively polyphenols, grape extracts, pine extracts, olive extracts (such as for example Manoliva™), marc extracts, N-acylated proteins, total N-acylated protein hydrolysates, amino acids, polyols such as glycerol or butylene glycol, urea, pyrrolidonecarboxylic acid or a derivative of this acid, glycyrrhetinic acid, alpha-bisabolol, sugars or sugar derivatives, polysaccharides or derivatives thereof, hydroxy acids, vitamins, vitamin derivatives (such as, for example, Sepivital™), enzymes, co-enzymes (such as, for example, Coenzyme Q10™), hormones or "hormone-like" substances (such as, for example, Phytoage™), plant extracts such as water melon extracts, bogbean extracts, extracts rich in tanins, aquatic mint extracts, soft water or sea water algal extracts, essential waxes, bacterial extracts, minerals such as, for example, mixed potassium and magnesium aspartate, lipids such as ceramides or phospholipids, hydroquinone, arbutin, kojic acid, active agents having antimicrobial activity such as Lipacide™ C8G, Lipacide™ UG, Octopirox™, Sensiva™ SC50 or Sepicontrol™ A5, the calming active agents described in U.S. Pat. No. 6,296,859, active agents having an energizing or stimulant property (for example Physiogenyl™ or Sepitonic™ M3), panthenol and derivatives thereof (such as Sepicap™ MP), or minerals (Givobio™ range or else Sepitonic™ M3).

The invention will be illustrated through reading the following nonlimiting examples.

EXAMPLE 1

Method for Preparing Xylityl Glucoside 703.0 g of xylitol are introduced into a glass reactor equipped with a jacket through which circulates a heat transfer fluid, and equipped with an effective stirring device.

The xylitol is melted at a temperature of 135° C., and the viscous paste thus obtained is cooled to 115° C.

Glucose is then added gradually to the reaction medium so as to allow it to disperse homogeneously.

An acid catalytic system consisting of 1.29 g of 96% sulfuric acid is added to the mixture thus obtained.

The reaction medium is placed under a partial vacuum of 90 mbar to 45 mbar, and kept at a temperature of 100° C.-105° C. for a period of 4 h 30 min with evacuation of the water formed by means of a distillation assembly.

The reaction medium is then cooled to 95° C.-100° C. and neutralized by adding 5 g of sodium hydroxide at 30%, so as to bring the pH of a solution containing 1% of this mixture to a value of 5.0.

The characteristics of the mixture thus obtained are as follows:
appearance (visual): orange wax at ambient temperature;
pH solution at 1%: 5.0;
residual xylitol: 55.8%;
residual glucose: <1%.

EXAMPLE 2

Method for Preparing Erythrityl Glucoside 300 g of erythritol are introduced into a glass reactor equipped with a jacket through which circulates a heat transfer fluid, and with an effective stirring device.

The erythritol is melted at a temperature of 145° C.

405 g of additional erythritol are dispersed in the viscous paste thus obtained and kept at 145° C. with stirring.

The reaction medium thus obtained is kept at 135° C.-140° C. for a period of 30 min, with stirring, and then 173.4 g of anhydrous glucose are dispersed in this reaction medium until a fluid and homogeneous medium is obtained.

The temperature is then brought back to 125° C.-130° C., and a catalytic system consisting of 1.61 g of 96% sulfuric acid is then introduced.

The reaction medium is placed under a partial vacuum, of between 45 mbar and 65 mbar, and kept at a temperature of 125° C.-130° C. for a period of 4 h 30 min with simultaneous evacuation of the water formed by means of a distillation assembly.

The reaction medium is then cooled to approximately 80° C. and neutralized by adding 6 g of a 30% sodium hydroxide solution so as to bring the pH of a solution containing 1% of this mixture to a value of 4.85.

The mixture thus obtained has the following characteristics:
appearance (visual): viscous orangey liquid;
pH of a solution at 1%: 4.85;
residual water: 1.4%;
residual erythritol: 0.4%;
residual glucose: <1%.

COMPARATIVE EXAMPLE

Method for Preparing Glyceryl Glucoside 1650.0 g of glycerol are introduced into a glass reactor equipped with a jacket through which circulates a heat transfer fluid, and equipped with an effective stirring device.

The glycerol is brought to 80° C. and 646.0 g of anhydrous glucose are gradually dispersed until a fluid and homogeneous medium is obtained.

The reaction medium is kept at 85° C. for a period of 30 minutes, with stirring, and then 4.65 g of 98% sulfuric acid are introduced.

The reaction medium is then brought to 100° C., placed under a partial vacuum of between 60 and 30 mbar, and maintained for 4 hours with concomitant evacuation of the water formed in situ by the reaction.

The reaction medium is then cooled to approximately 80° C. and neutralized by adding 24 g of a 30% sodium hydroxide solution so as to bring the pH of a solution containing 1% of this mixture to a value of 6.1.

The composition thus obtained has the following characteristics:
appearance (visual): viscous yellow liquid;
pH solution at 1%: 6.1
residual glycerol: 42.4%
residual glucose: <1%

Demonstration of the Properties of the Polyol-Glycosides that are Useful According to the Invention The moisturizing properties of the polyol-glycosides that are useful in the context of the invention were demonstrated:
firstly, by in vivo measurement of the moisturization of the skin in a normal volunteer by means of a device known as Hydrascan®; and
secondly, by in vitro measurement of the effect of the polyol-glycosides on the production of hyaluronic acid, a compound of the glycosaminoglycan family capable of attaching up to one thousand times its weight in water.

A—In Vivo Measurement of the Moisturization of the Skin in a Normal Volunteer by Means of Hydrascan®

The effect on the degree of moisturization of the skin of various polyol-glycosides according to the invention, of glyceryl glucoside and of various polyols was measured and compared in humans.

a) Principle of the Method

The degree of moisturization of the skin is measured using the device sold under the name Hydrascan®.

This device, which is well known to those skilled in the art, makes it possible to measure transient thermal transfer, a parameter similar to thermal effusivity, which is a property possessed by a body that exchanges heat with another body with which it is brought into contact.

This device comprises a micro-effusimeter connected to a flexible sensor and makes it possible to produce a thermal wave which propagates within the epidermis, and to register the variation in temperature during the pulse.

The setting of the device makes it possible to measure the degree of moisturization at three depth levels in the epidermis:
Cycle 1: stratum corneum and superficial epidermis;
Cycle 2: superficial epidermis and middle epidermis;
Cycle 3: the entire epidermis.

The measurements carried out by means of this device therefore make it possible to explore the superficial layers of the skin and to thus measure the degree of moisturization of the skin throughout the entire epidermis.

b) Products Tested

The products tested were formulated in the form of a cream gel containing:
3% (weight/volume) of the test product;
2% (weight/volume) of Sepigel® 305 (polyacryl-amide/$C_{13}$-$C_{14}$ isoparaffin/laureth-7);
5% (weight/volume) of Lanol® 99 (isononyl isononanoate);
0.5% (weight/volume) of Sepicide® HB (phenoxy-ethanol, methyl-, ethyl-, propyl-, butylparaben).

A cream gel having the same composition but containing no test product is used as a placebo.

The degree of moisturization of the skin was thus measured and compared for the following products:
glucose, xylose, glycerol, xylitol, erythritol, product of example 1, product of example 2, product of the comparative example.

c) Experimental Protocol

The study is carried out on three groups of six volunteers, as a double-blind study, i.e. neither the experimenter nor the volunteer knows the identity of the test product.

The following four skin zones are defined on the forearms of each volunteer:
a zone treated with a polyol-glucoside;
a zone treated with the corresponding polyol;
a zone treated with the placebo common to all the products;
an untreated zone.

The products are applied topically at a rate of 20 mg/cm$^2$, the measurements being carried out 8 h after application.

To avoid undesirable variations in the measurements, the volunteers are placed in a temperature-controlled (25° C.± 2° C.) and hygrometry-controlled (50%±4%) room for at least 30 min.

The degree of moisturization is measured by means of Hydrascan®, on each skin zone defined above, the values obtained for each of the three cycles being recorded and expressed as percentage increase in moisturization of the skin relative to the zone treated with the placebo. These values correspond to the mean obtained for the six volunteers.

d) Results Obtained

| Product | Degree of moisturization of the skin measured with Hydrascan ® | | |
| --- | --- | --- | --- |
| | Cycle 1: stratum corneum + superficial epidermis | Cycle 2: superficial + middle epidermis | Cycle 3: entire epidermis |
| Glucose | <5% | <5% | <5% |
| Xylose | <5% | <5% | <5% |
| Glycerol (3 OH) | +14% | +13% | +13% |
| Erythritol (4 OH) | +9% | +9% | +9% |
| Xylitol (5 OH) | <5% | <5% | <5% |
| Comparative example | <5% | <5% | <5% |
| Example 2 | +18% | +11% | +12% |
| Example 1 | +28% | +33% | +30% | e) Analysis of the Results—Conclusions

The results, reported in the above table, show that glycerol increases the degree of moisturization of the superficial and middle layers of the epidermis and also of the entire epidermis. The increase is comparable whatever the epidermal layer studied.

On the other hand, this increase is very substantially reduced when the glycerol is etherified with glucose (product of the comparative example).

Glucose and xylose alone exhibit no moisturizing effectiveness.

The xylitol (polyol having five hydroxyl groups) has no effect on the degree of moisturization of the various layers of the epidermis. On the other hand, the xylityl glucoside (product of example 1) very substantially increases the degree of moisturization of the superficial and middle layers of the epidermis and also of the entire epidermis. The increase is greater, of the order of 14 to 20%, than that obtained with glycerol.

Erythritol (polyol having four hydroxyl groups) increases the degree of moisturization of the superficial and middle layers of the epidermis and also of the entire epidermis. However, the effect is less substantial than that obtained with glycerol. On the other hand, this increase is amplified when the erythritol is in the form of erythrityl glycoside (product of example 2).

In conclusion, this study:
shows the moisturizing capacity of glycerol and of erythritol and confirms that this moisturizing capacity decreases when the number of hydroxyl groups of the polyol increases;

demonstrates the very strong moisturizing potential of the xylityl glucoside and, to a slightly lesser degree, that of the erythrityl glucoside. These two moisturizing potentials are greater than that of the glycerol and of the glyceryl glucoside.

B—In Vitro Measurement of the Effect of the Polyol-Glycosides According to the Invention on the Production of Hyaluronic Acid To confirm the moisturizing activity of the polyol-glycosides according to the invention, the effect of these products on the amount of hyaluronic acid was measured. It is in fact known that hyaluronic acid is a major non-sulfated glycosaminoglycan which plays an essential role in moisturizing the skin, by means of its ability to attach up to 1000 times its weight in water.

a) Principle of the Method

The amount of hyaluronic acid is measured in normal human dermal fibroblast cultures.

The cells are incubated for 5 days in the presence of the test products solubilized in the incubation medium.

At the end of this incubation, the extracellular media, into which the hyaluronic acid is secreted, are removed.

The hyaluronic acid is stained with a specific dye, STAINS ALL ((1-ethyl-2-[3-(1-ethylnaphtho[1,2-d]thia-zolin-2-ylidene)-2-methylpropenyl]naphtho[1,2-d]thia-zolium)bromide, provided by Sigma), which interacts with the hyaluronic acid to produce a change of absorption spectrum between 620 and 660 nm, observed by means of a spectrophotometer. A standard range of hyaluronic acid is effected in parallel.

b) Products Tested

The polyols and the polyol-glucosides are tested in aqueous solution at 0.01% and 0.1% (w/v).

The polyols tested are glycerol, xylitol and erythritol. The polyol-glucosides tested are glyceryl glucoside (product of the comparative example), xylityl glucoside (product of example 1) and erythrityl glucoside (product of example 2).

c) Experimental Protocol:

This can be summarized by means of the following diagram:

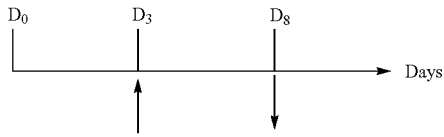

in which D0, D3 and D8 have the following meanings:

D0: seeding of the fibroblasts (24-well culture plates, 15 300 cells/well);

D3: incubation of the products tested, diluted in the fibroblast incubation medium;

D8: removal of the fibroblast incubation media, assaying of the hyaluronic acid.

At the end of the 5 days of incubation in the presence of the products, the incubation media are removed and incubated in the presence of STAINS ALL. The colorimetric reaction is visualized by adding water.

The quantification is carried out by spectrophotometry for a wavelength of 630 nm.

A standard range of hyaluronic acid (0 to 12.5 µg/ml) is effected in parallel.

The results are expressed in µg/ml of extracellular hyaluronic acid.

d) Results Obtained:

The results which were obtained, expressed as percentage increase in the amount of extracellular hyaluronic acid relative to the control group, are reported in the following table:

| Product | Concentration (%, w/v) | |
|---|---|---|
| | 0.01 | 0.1 |
| Glucose | <10% | <10% |
| Glycerol | <10% | <10% |
| Erythritol | <10% | <10% |
| Xylitol | <10% | <10% |
| Product of the comparative example | <10% | <10% |
| Product of example 2 | +64% | <10% |
| Product of example 1 | +158% | +161% | e) Analysis of the Results—Conclusions

After 5 days of incubation in the presence of the fibroblasts, none of the polyols tested increases the amount of extracellular hyaluronic acid.

The glyceryl glucoside (product of the comparative example) does not increase the amount of extracellular hyaluronic acid.

The xylityl glucoside (product of example 1), and to a lesser degree, the erythrityl glucoside (product of example 2), increase the amount of extracellular hyaluronic acid.

Among the three polyol-glucosides tested, the xylityl glucoside (product of example 1) is the most effective.

The three polyols tested, glycerol, xylitol and erythritol, have no effect on the extracellular amount of hyaluronic acid.

Among the three polyol-glucosides tested, glyceryl glucoside, xylityl glucoside and erythrityl glucoside, the xylityl glucoside very markedly increases the extracellular amount of hyaluronic acid. The erythrityl glucoside also increases this parameter, to a less substantial degree. This in vitro model makes it possible to select the xylityl glucoside as being the most advantageous product; this classification is similar to that obtained in the in vivo test.

The restructuring properties of the polyol-glycosides that are useful in the context of the invention were demonstrated by in vitro measurement of the effect of the polyol-glycosides, in particular the xylityl glucoside, on the synthesis of ceramide 1 and ceramide 2, which are compounds of the family of epidermal lipids which play a key role in the barrier function of the skin.

C—In Vitro Measurement of the Xylityl Glucoside According to the Invention on the Synthesis of Epidermal Ceramides To illustrate the increase in cellular cohesion of the skin by means of the polyol-glycosides, in particular by means of the xylityl-glucoside according to the invention, the effect of these products on the synthesis of ceramide 1 and of ceramide 2 was measured in comparison with glycerol and compounds known by those skilled in the art to increase this synthesis.

a) Principle of the Method

The study is carried out in vitro in a human skin explant model. The products, formulated at 3% in a cream gel, are applied to the surface of the skin explants for 24 hours. The neosynthesis of the epidermal lipids is studied by radioactive labeling (carbon 14-labeled acetate) of the neosynthesized lipids, followed by thin layer chromatography to separate the various types of lipids and in particular the ceramides.

b) Products Tested

The xylityl glucoside according to example 1 of the invention, formulated at 3% in a cream gel comprising 2% of Sepigel® 305, 5% of Lanol 99, and qs of water.

Glycerol formulated at 3% in the same cream gel.

Epidermal growth factor (EGF), known to increase the synthesis of ceramides, which constitutes a reference molecule for this test. The EGF is tested at 10 ng/ml in the skin explant culture medium.

A placebo corresponding to the cream gel.

A commercially available formulation containing lactic acid, which constitutes a reference for the test, lactic acid being known to increase the synthesis of ceramides.

c) Experimental Protocol

The study is carried out on disks of human skin originating from cosmetic surgery (abdominoplasty, 35-year-old caucasian woman). Disks 8 mm in diameter are produced using a hole punch and deposited onto culture inserts placed in culture wells containing an appropriate nutritive medium (MEM/M199 medium (¾, ¼, v/v) supplemented with penicillin (50 IU/ml, streptomycin (50 µg/ml), sodium bicarbonate (0.2% w/v), serum (2% v/v) and carbon 14-labeled acetate (1 µCi/ml)).

The products are tested by topical application (except for the EGF) for 24 hours.

At the end of the 24 hours of incubation, the skin explants are rinsed with phosphate buffered saline. For each disk of skin, the dermis is dissociated from the epidermis by controlled heat shock (1 min at 70° C.). The epidermal lipids are extracted by a partition between an organic phase (methanol/chloroform (1:2)) and an aqueous phase (0.25 M potassium chloride). The organic phase is then evaporated under vacuum and the residue is taken up in a chloroform/methanol (2:1) mixture.

The various epidermal lipids are then separated by thin layer chromatography (silica 60): chloroform/acetone/methanol (38:2:10); chloroform/acetone/methanol (40:5:5); chloroform/ethyl acetate/diethyl ether/methanol (36:10:3:1). The radioactivity of the fractions thus separated is counted with a radioactivity analyzer (Storm, Amersham).

The results are expressed as % variation relative to the control group.

d) Results Obtained

The results which were obtained, expressed as percentage increase in the amount of ceramide 1 and of ceramide 2 relative to the control group, are reported in the following table:

|  | EGF | Formulation with lactic acid | Xylityl glucoside according to example 1 | Glycerol | Placebo |
| --- | --- | --- | --- | --- | --- |
| Ceramide 1 | 166.1% | 158.5% | 295.7% | 114.9% | 174.6% |
| Ceramide 2 | 152.3% | 125.6% | 236.5% | 151.7% | 169.9% | e) Analysis of the Results—Conclusion

The use of the xylityl glucoside in the cream gel significantly increases the neosynthesis of ceramides 1 and 2, which is not observed in the presence of glycerol or of the placebo in the same formulation scheme.

The EGF and the formulation containing lactic acid, known by those skilled in the art to possess an action on the increase in neosynthesis of ceramides 1 and 2, act, but less effectively than the composition derived from example 1 of the invention.

These effects on the ceramides reflect a restructuring effect of the xylityl glucoside on the skin barrier, which is, moreover, in agreement with the moisturization measurements carried out in vivo in the various layers of the epidermis.

These results are in agreement with long-term moisturizing effects of the xylose-glucoside.

Demonstration of the Skin Tolerance of the Polyol-Glycosides that are Useful According to the Invention The skin tolerance of the various polyol-glycosides was evaluated by means of a study of "evaluation on the skin of acute skin irritation", carried out by an independent pharmaceutical and cosmetic consultancy-expertise company.

The Primary Cutaneous Irritation (PCI) index measurements, carried out according to the same protocol, are contained in the following table:

|  | IRRITATION | |
| --- | --- | --- |
| Product | PCI index | Classification |
| Xylityl glucoside (example 1) | 0 | Nonirritant |
| Erythrityl glucoside (example 2) | 0 | Nonirritant |
| Glyceryl glucoside (comparative example) | 0 | Nonirritant |

Each compound studied is classified, in view of the results obtained under the selected experimental conditions, nonirritant for the skin, with reference to the scale proposed in the protocol described in the *Journal Officiel de la République Française [Official Journal of the French Republic]* of Feb. 21, 1982.

These novel polyol-glycoside compositions (examples 1 and 2) do not therefore induce any modification in skin tolerance compared with the comparative example relating to a prior state of the art.

Some examples of compositions having moisturizing activity according to the invention will now be given.

EXAMPLE 3

Moisturizing Body Milk

Formula

| | | |
| --- | --- | --- |
| A | Water | QS 100% |
| | Fucogel | 03.00% |
| | Micropearl ™ M305 (methyl methacrylate cross-polymer) | 05.00% |
| | Moisturizing active agent | 03.00% |
| | Montanov ™ L ($C_{14}$-$C_{22}$ alcohol & $C_{12}$-$C_{20}$ alkyl glucoside) | 04.00% |
| B | Lanol ™ 99 (isononyl isononanoate) | 04.00% |
| | Simulgel ™ EG (sodium acrylate sodium acryloyl-dimethyl taurate copolymer/isohexadecane/sorbitan oleate) | 01.00% |
| C | DC345 (cyclomethicone) | 12.00% |
| D | Fragrance | qs. |
| | Sepicide ™ HB (phenoxyethanol/methylparaben/ethylparaben/propylparaben/butylparaben) | 00.30% |
| | Sepicide ™ CI (imidazolidinyl urea) | 00.20% |

Procedure:

the fatty and aqueous phases (B and A) are heated separately to 75° C.-80° C.,

B is emulsified in A with stirring by means of a rotor-stator turbine,

C is added and the mixture is maintained for a few minutes with vigorous stirring, the mixture is cooled with moderate stirring, D is added at 30° C.

EXAMPLE 4

Moisturizing Cream-Gel

Formula

| A | Water | qs 100% |
|---|---|---|
|   | Glycerol | 02.50% |
|   | Micropearl ™ M305 | 01.00% |
|   | Sepicide ™ CI | 00.20% |
|   | Moisturizing active agent | 02.00% |
| B | Simulgel ™ EG | 01.00% |
| C | Lanol ™ 99 | 05.00% |
|   | DC345 | 02.50% |
|   | Sepicide ™ HB | 00.30% |
|   | Fragrance | qs. |

Procedure:
the Micropearl™ M305 is dispersed at ambient temperature in the water/glycerol/moisturizing active agent/Sepcide™ CI mixture,
phase A prepared according to the method mentioned above is added to B gradually, homogenizing the preparation after each addition with moderate stirring,
C is added to the gel prepared above.
Characteristics: Appearance: brilliant white gel; pH=6.2.

EXAMPLE 5

Moisturizing Energizing Body Water

Formula:

| A | Fragrance | qs. |
|---|---|---|
|   | Oramix ™ CG 110 | 02.50% |
|   | Sepicide ™ HB | 00.50% |
| B | Glycerol | 01.00% |
|   | Moisturizing active agent | 1.00% |
|   | Sepitonic ™ M3 | 01.00% |
|   | Sepicide ™ CI | 00.30% |
|   | Water | qs. 100% |

Procedure:
the fragrance and the Sepicide™ HB are solubilized in the Oramix™ CG 110 in order to prepare A,
the ingredients of B are added in the order indicated at ambient temperature with moderate stirring.
Characteristics: Appearance: clear translucent and colorless liquid; pH=5.

EXAMPLE 6

Energizing Shower Gel

Formula

| A | Moisturizing active agent | 03.00% |
|---|---|---|
|   | Sepicide ™ HB | 00.30% |
|   | Fragrance | qs. |
|   | Montanox ™ 81 (polysorbate 81) | 02.00% |
| B | Proteol ™ OAT (sodium lauroyl OAT amino acids) | 05.00% |
|   | 28% sodium lauryl ether sulfate | 45.00% |
|   | Sepitonic ™ M3 | 01.00% |
|   | Sepicide ™ CI | 00.30% |
|   | Water | qs. 100% |

| Montaline ™ C40 (cocamidopropylalbetainamide MEA chloride) | 05.00% |
|---|---|
| Sodium chloride | 00.75% |
| Lactic acid | qs. pH |

Procedure:
the ingredients of phase A are mixed at ambient temperature with moderate stirring,
the ingredients of phase B are added in the order indicated, under the same operating conditions.
Characteristics: Appearance: clear gel; pH=

EXAMPLE 7

Moisturizing Lipstick

Formula:

| A | Castor oil | qs. 100.00% |
|---|---|---|
|   | Cera alba (beeswax) | 07.50% |
|   | Candellila wax | 07.50% |
|   | Cera microcristallina | 15.00% |
|   | Sepifeel ™ One (palmitoylproline/magnesium palmitoyl glutamate/sodium palmitoyl sarcosinate-Seppic) | 03.00% |
|   | Sepilift ™ DPHP (DiPalmitoylHydroxyProline-Seppic) | 01.00% |
|   | Cetyl alcohol | 01.50% |
|   | Isopropyl lanolate | 01.00% |
|   | Cetyl ricinoleate | 00.80% |
|   | Micropearl ™ M 310 (crosslinked PMMA, distributed by Seppic) | 02.00% |
|   | Butyrospermum parkii (karite butter) | 03.00% |
|   | Paraffinum liquidum | 02.50% |
|   | Lanol ™ 1688 (cetearyl octanoate - Seppic) | 02.50% |
|   | Caprylic/capric triglyceride | 04.00% |
|   | Carnauba wax | 03.50% |
|   | CI 77491 | 01.40% |
|   | CI 45410-DC red 27 | 00.10% |
|   | CI 77891-titanium dioxide | 11.00% |
|   | Perfluoromethyl isopropyl ether | 00.10% |
| B | Montane ™ 80 | 47.50% |
|   | Water | qs. 100.00% |
|   | Moisturizing active agent | 05.00% |
|   | Sepicide ™ CI | 00.20% |
|   | Sepicide ™ HB | 00.30% |

Procedure:
phase A is prepared in a three-cylinder mill, by adding each compound, prepared beforehand, in molten form,
phase B is added at 80° C. with moderate stirring, until a homogeneous dispersion on the molten phase is obtained,
the mixture is then poured into molds suitable for the molding.

What is claimed is:
1. A method for restructuring the epidermis with a composition, by topically administering to a subject in need thereof an effective amount of said composition, wherein said composition comprises a xylityl-glycoside, wherein said xylityl-glycoside is obtained by the acetalization of xylitol with a reducing sugar selected from the group consisting of:
a) glucose;
b) xylose; and
c) arabinose.
2. The method of claim 1, wherein said xylityl-glycoside is xylityl glucoside.

* * * * *